United States Patent
Kwak et al.

(10) Patent No.: US 6,649,748 B1
(45) Date of Patent: Nov. 18, 2003

(54) **PEROXIDASE GENOMIC GENE DERIVED FROM *IPOMOEA BATATAS* AND A PROMOTER THEREOF**

(75) Inventors: Sang-Soo Kwak, Taejeon (KR); Haeng-Soon Lee, Taejeon (KR); Suk-Yoon Kwon, Taejeon (KR); Kee-Yeun Kim, Taejeon (KR)

(73) Assignee: Korea Research Institute of Bioscience and Biotechnology, Taejeon (KR)

( * ) Notice: Subject to any disclaimer, the term of this patent is extended or adjusted under 35 U.S.C. 154(b) by 0 days.

(21) Appl. No.: 09/744,900

(22) PCT Filed: Oct. 28, 2000

(86) PCT No.: PCT/KR00/01231

§ 371 (c)(1),
(2), (4) Date: Jan. 31, 2001

(87) PCT Pub. No.: WO01/31018

PCT Pub. Date: May 3, 2001

(30) Foreign Application Priority Data

Oct. 29, 1999 (KR) .......................................... 1999/47361
Oct. 18, 2000 (KR) .......................................... 2000/61231

(51) Int. Cl.[7] .......................... C12N 15/82; C12N 15/29
(52) U.S. Cl. ................................. 536/24.1; 435/320.1
(58) Field of Search ....................... 435/320.1; 536/24.1

(56) References Cited

U.S. PATENT DOCUMENTS 5,689,056 A * 11/1997 Cramer et al. .............. 800/205

OTHER PUBLICATIONS

Menke et al. A novel jasmonate and elicitor responsive element in the periwinkle secondary metabolite biosynthetic gene Str interacts with jasmonate and elicitor inducuble AP2 domain transcription factor ORCA2. 1999, The Plant Journal 18(16): 4455–4463.*

G.–H. Huh et al., "Molecular cloning and characterization of cDNAs for anionic and neutral peroxidases from suspensioncultured–cells of sweet potato and their differential expression in response to stress," Mol. Gen. Genet., 1997, 255:382–391.

K.–Y. Kim et al., "Molecular characterization of cDNAs for two anionic peroxidases from suspension cultures of sweet potato," Mol. Gen. Genet., 1999, 261:941–947.

* cited by examiner

*Primary Examiner*—David T. Fox
*Assistant Examiner*—Cynthia Collins
(74) *Attorney, Agent, or Firm*—Gates & Cooper LLP

(57) ABSTRACT

The present invention relates to a stress inducible promoter. Particularly, it relates to an *Ipomoea batatas* peroxidase isozyme gene promoter which is strongly induced under environmental stresses in cultured cells and whole plants. The promoter of the present invention can effectively be used to develop stress-tolerant plants which have resistance to environmental stresses, and to develop transformed organisms which can produce useful materials on a large scale.

5 Claims, 12 Drawing Sheets

FIG. 2a

```
                      ttaatttcaatattttgtctgtattttt     -1828
ttttagtactactcatgtcaaatcctgttacatataaatatgttcaaattcactgaaa  -1800
ctcaaatctataacctcttatttgatagagtcattctatacaactagaccacggaattgt -1740
caactagaccacggaattgttagcttgtttattgtattcacgtataattttgatgaatat -1680
catcaactttgacgggcaaaatagatagcatgtggcggccacagtttcaaaattcataca -1620
agatgtcaaggggaccggcccggtggctgcgtgcatatcacgtgcaagatttgtgaaatt -1560
cttttctagattccttttatcctttttcttcttttcttgaaaaaatagaaacagaaattatat -1500
gtaaataaaataataataatatggtttccatactctatagcatatcatatggtgcattgc -1440
acatatttcatcgacaaagaaagccacggtgcagacgctcgattttgacatttctacaact -1380
tacaaggccatgatcagatcgataataccaaatggtaccacctaactaggtgatatatat -1320
tatgtatgtcattattttaaactgtattacaaagactatttttttcattaattggtacaaa -1260
gaaaattaaacagaaagaaaggaaagaatgactcaccacctagcacctagacacctag -1200
acaccaagtacccaaaccctctatttttcaacatctattttcagatgtaaatatgagttgg -1140
acgaagaaggtgttagcaattatttgattaatcttgctacgataattatgatccacctcac -1080
ttagtcattttttttcagaccaagacaactagcttgagttttttattgtatgtggtcggaa -1020
cgtttttttgtaattaaaaaataaaagttgcatcattatatatggtagattaagtaattg  -960
atcaatcaacgtttaattttttgcatttatcggcaaggtggagattcaacttccagtcgaa  -900
cttagagagtcattggagaccttgaccagttaactagcggtgtcgaaaacctgcacaact  -840
tgagattctaattgcatacctttatatatgacgcgtttttatttttttttcctagaaaata  -780
atttggaagaaaataagaatatgtattctgtgaaagctaggccaaaacgaatgtcttttc  -720
gtcgttttcgttaaaggtttagatcatatttcatctggtcaacactcaaacttgtataa  -660
tggacgaattattagtcatttttagacctaccggctagcgcgactttttttgttttccataa  -600
agatccgataattgcatggccagatgcaaagtttgaaatttaatgtttgccaaatcctat  -540
catacaccacaacacatgtctcagggccaagtggcaccagcaaacatccctgtcataatt  -480
aatttttttaatgagaaggaggaaactcacagctattactcgaaggtatataatattgag  -420
taaatcttactttgtgattctagttgacaaaacaccgcaagataaactatactaagttca  -360
aatcacctcaccgggttggctcagattggttttttcaatacaagagggggtgtgaactcc  -300
cgtgccgacctctttttgagggacaataatgtacggtcacgccaaccaagcttgatttttt  -240
atgacaaatatattactacatatattacacggtcaaataattaatcaaaaaataaaaaaa  -180
gaccccaattaaagtccccaaccactctcaaatattctatttaagggaaaccttagaggc  -120
aattcatgcatcctcaaccccttctcctcatttttttaatcttacatttttccttttgacc   -60
ATGGCTTCCATTGTGAGTCGGCTCAGTCTTGCGCTAAGCCTCATAGCTCTAGCTCTAGCT   +60
 M  A  S  I  V  S  R  L  S  L  A  L  S  L  I  A  L  A  L  A
GGCTACTCCATTTACCAGCACACACAGTCAGCCATGGAGAGCCAGCCCATCAAGGCTCTC  +120
 G  Y  S  I  Y  Q  H  T  Q  S  A  M  E  S  Q  P  I  K  A  L
CCGGCGTGGCTACAGCTCCCCACGTTCCAATCTGCCAACGTGTTATCGTATTATCCGAGT  +180
 P  A  W  L  Q  L  P  T  F  Q  S  A  N  V  L  S  Y  Y  P  S
GGCCGCAAATCCTCCCCCGCCGGCATGCTTTCCGACGAAGCTTGCGTGTTCTCCGCCGTT  +240
 G  R  K  S  S  P  A  G  M  L  S  D  E  A  C  V  F  S  A  V
AAAGAAGTTGTCGACGCCGCCATCGATAACGAAACTCGCATGGGGGCTTCCCTCATTCGT  +300
 K  E  V  V  D  A  A  I  D  N  E  T  R  M  G  A  S  L  I  R
CTCTTCTTCCACGATTGCTTTGTCGATgtacgtatagtatacatataattatgtaaaacc  +360
 L  F  F  H  D  C  F  V  D
tatatatatatatatatatatatatatacatgcacaaaagtttataatactaatatata   +420
```

FIG. 2b

```
cccatactttttgcatatcattatatatattaacacgattatattaaaaccaataatat    +480
attatatatatatatagttaactatctttttcttttcacttttcttatcactttttaaatt  +540
gttaatctaaaaatcaattgttattttattgaatctttttctattrcctattctgtttaa   +600
agacttaattatactattatttaactgggctggtaactttccgtcaatattgtttattta   +660
acaattgtaacaattaaaaccaattgtaacaatagtacgtaaaagatcaaagtgacatau   +720
accagcttaagttttttaatggacgaactcaaaacaaaaaagtcaatatgtaatttcgg   +780
tagagaagtcaaatttaaaattttcatagttatcaaatcaattgttttatcaaccagcta  +840
ggttgnctattcaaaaactaattagacattggtgtgcatgaaacattacgttaaaacaa   +900
aagttatcacccacctcgtcttataattggtgtacctaagttatcacacgtccctgtcga  +960
acttacacgccaaacatgtcaatatgtcaaatgctttaatgaaaaatattattagattac  +1020
tatttatctaatactaaattttcttccttcgtaaaaattgtgtgtattaGGTTGTGATGC  +1080
                                                G  C  D  A
AGGGCTTCTTTTGAATGATACGGCGACGTTCACAGGGGAACAAACTGCATTTGGCAATCT  +1140
 G  T  T   T  N  D  T  A  T  F  T  G  E  Q  T  A  F  G  N  L
TAATTCCGTGAGAGGGTTTGAGGTTATAGAACAAGCTAAACAGAATGCAGTAGCTAAATG  +1200
  N  S  V  R  G  F  E  V  I  E  Q  A  K  Q  N  A  V  A  K  C
TGCCGATACACCCGTATCTTGTGCTGACATTTTATCTATTGCTGCTCGTGATTCTTTCGA  +1260
   A  D  T  P  V  S  C  A  D  I  L  S  I  A  A  R  D  S  F  E
ACGGgtaagtcttcaatatcgtgtataagtgttactaataatgtcaatatgttacatgta  +1320
 R
gacatgtatttattctattttcttgtattttacattcaacagTTTAGTGGAGCAACATACA +1380
                                           F  S  G  A  T  Y
CTGTGACTTTAGGGCGACTCGATGCGAGAACCGCGAACTTAACCGGAGCTAATACCCAGC  +1440
  T  V  T  L  G  R  L  D  A  R  T  A  N  L  T  G  A  N  T  Q
TTGTCGGACCATCGGAAAACTTGACTGAACAAGTCAGGAAATTTGGCATCAAAGGATTTA  +1500
  L  V  G  P  S  E  N  L  T  E  Q  V  R  K  F  G  I  K  G  F
ACGAGAGGGAATTGGTCGCCTTGTTGGCTTCACACACGCTAGGGTTTGCCAGATGTCCGG  +1560
  N  E  R  E  L  V  A  L  L  G  S  H  T  L  G  F  A  R  C  P
TTTTATGTGACAACAGAAACATTAACCCGGTTCGGGTCCCCGGTCTGCAATGCAACTGTC  +1620
  V  L  C  D  N  R  N  I  N  P  V  R  V  P  G  L  Q  C  N  C
CTGTAACTAATACTGACCCGGGTTTGGTCGGGCTGGACCCCACACCCGATACATTCGACC  +1680
  P  V  T  N  T  D  P  G  L  V  G  L  D  P  T  P  D  T  F  D
AACGTTATTACTCTGACCTAGTCAGCGGCCAAGGCCTCCTGTTTTCCGACCAACAGCTGA  +1740
  Q  R  Y  Y  S  D  L  V  S  G  Q  G  L  L  F  S  D  Q  Q  L
TGAACAGCACCACCACCAGCGACGCCGTGACGACCTACCGTGACTCCATAGACACCTTCC  +1800
  M  N  S  T  T  T  S  D  A  V  T  T  Y  R  D  S  I  D  T  F
TTGCCGACTTCGCCGCCGCCATGGTCAAGATGAGCAACCTGCCTCCGTCCGCCGGAGTTG  +1860
  L  A  D  F  A  A  A  M  V  K  M  S  N  L  P  P  S  A  G  V
AGCTCGAAATCCGTGACGTCTGCAGCCGGGTGAATGACGTCTCTGTTGCATCC         +1913
  E  L  E  I  R  D  V  C  S  R  V  N  D  V  S  V  A  S
```

FIG. 3

```
                                  ttaatttcaatatttcgtctgtatttttt  -1828
ttttcagtactactcatgtcaaatcctgttacatataaaatatgttcaaattcactgaaa  -1800 ctcaaatctataacctcttatttgataqagtcactctatacaactagaccacggaattgt  -1740
                        GCN4
caactagaccacggaattgttagcttgtttattgtattcacgtataattttgatgaatat  -1680
catcaacttctgacgggcaaaatagatagcatgtggcggccacagtttcaaaattcataca  -1620
agatgtcaaggggaccggcccggtggctgcgtgcatatcacgtgcaagatttgtgaaatt  -1560
ctttctagattcctttatcctttctttctttcttgaaaaaatagaaacagaaattatat  -1500
gtaaataaaataataatatggtttccatactctatagcatatcatatggtgcattgc    -1440 acatatttcatcgacaaagaaagccacggtgcagacgctcgattttgacattttacaact  -1380
tacaaggccatgatcagatcgataataccaaatggtaccacctaactaggtgatatatat  -1320
tatgtatgtcattatttttaaactgtattacaaagactatttttcattaattggtacaaa  -1260
     oct-1
gaaaaattaaacagaaaagaaaggaaaaaaatgactcaccacctagcacctagacacctag  -1200
              HSTF           GCN4    AP-1
acaccaagtacccaaaccctctatttcaacatctatttcagatgtaaatatgagttgg    -1140
acgaagaaggtgttagcaattatttgattaatcttgctacgataattatgatccactcac  -1080 ttagtcattttttcagaccaagacaactagcttgagttttttattgtatgtggtcggaa  -1020
 AP-1
cgttttttgtaattaaaaaataaaagttgcatcattatatatggtagattaagtaattg    -960
                                              CCAAT/enhancer
atcaatcaacgtttaatttgcatttatcggca?ggtggaggttccaacttccagtcgaa   -900
CAAT box
cttagagagtcattggagaccttgaccagttaactagcggtgtcgaaaacctgcacaact  -840
   GCN4
tgagatttaattgcataccttttatatatgacgcgttttattttttttcctagaaaata   -780
                 TATA box
atttggaagaaaataagaatatgtattctgtgaaagctaggccaaaacgaatgtcttttc  -720 gtcgttttcgttaaaggtttagatcatatttcatctggtccaacactcaaacttgtataa  -660
tggacgaattattagtcattttagacctaccggctagcgcgacttttttgttttccataa  -600
                      motif-P
agattcgataattgcatggccagatgcaaagtttgaaatttaatgtttgccaaatcctat  -540
catacaccacaacacatgtctcaggqccaagtggcaccagcaaacattcctgtcataatt  -480
                     G-box
aatttttttaatgagaaggaggaaactcacagctattactcgaaggtatataatattgag  -420
taaatcttactttgtgattctagttgacaaaacaccgcaagataaactatactaagttca  -360
aatcacctcaccgggttggctcagattggttttttcaatacaagaggggtgtgaactcc  -300
                                          SP-1
cgtgccgacctcttttgagggacaataatgtacggtcacgccaaccaagcttgatttttt  -240
ctgacaaatatattactacatatattacacggtcaaataattaatcaaaaaataaaaaaa  -180 gacccccaattaaagtccccaaccactcttaaatattctatttaagggaaaccttagaggc  -120 aattcatgcatcctcaaccccttcttcttcattttcttaatcttacattttcctttgacc   -60
ATGGCTTCCATTGTGAGTCGGCTCAGTCTTGCGCTAAGCCTCATAGCTCTAGCTCTAGCT   -60
 M  A  S  I  V  S  R  L  S  L  A  L  S  L  I  A  L  A  L  A
```

FIG. 7
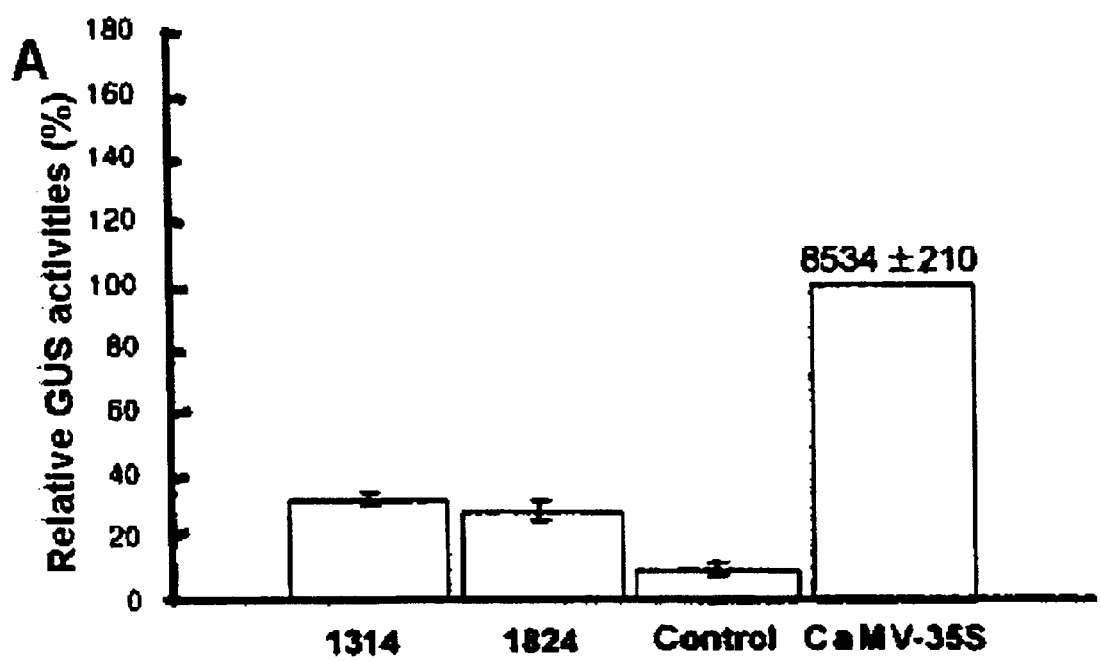
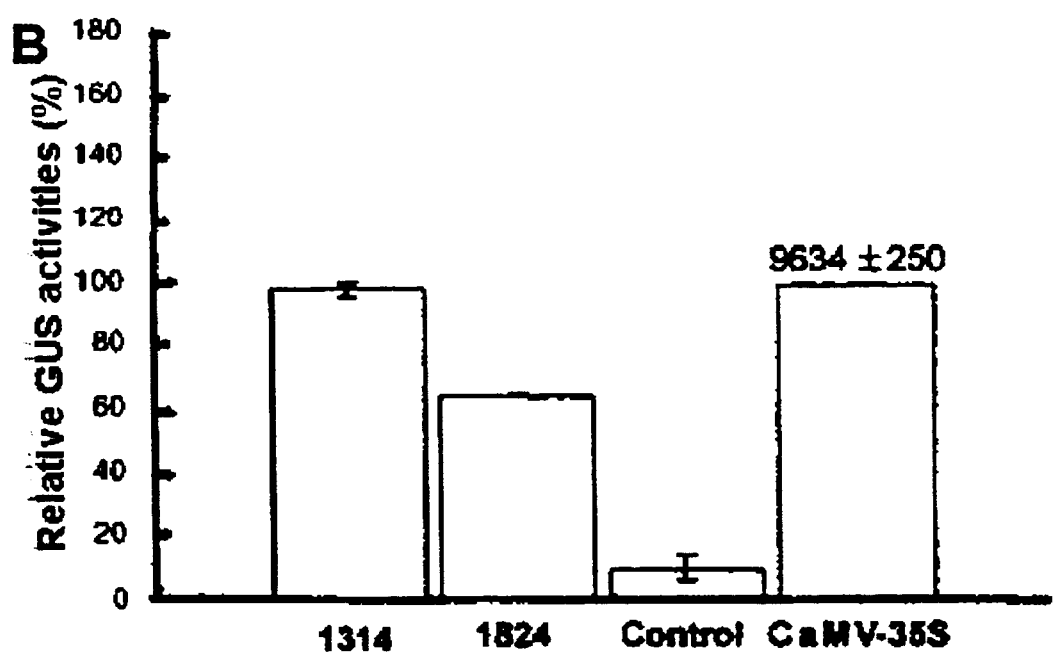

SEQUENCE LISTING

<160> NUMBER OF SEQ ID NOS: 13

<210> SEQ ID NO 1
<211> LENGTH: 3742
<212> TYPE: DNA
<213> ORGANISM: Imopoea batatas
<220> FEATURE:
<221> NAME/KEY: misc_feature
<222> LOCATION: (0)...(0)
<223> OTHER INFORMATION: n = a, t, c, or g

<400> SEQUENCE: 1

```
ttaatttcaa tattttgtct gtattttttt tttagtacta ctcatgtcaa atcctgttac      60
atataaaata tgttcaaatt cactgaaact caaatctata acctcttatt tgatagagtc     120
actctataca actagaccac ggaattgtca actagaccac ggaattgtta gcttgtttat     180
tgtattcacg tataattttg atgaatatca tcaactttga cgggcaaaat agatagcatg     240
tggcggccac agtttcaaaa ttcatacaag atgtcaaggg gaccggcccg gtggctgcgt     300
gcatatcacg tgcaagattt gtgaaattct ttctagattc cttttatcct tttcttcttt     360
cttgaaaaaa tagaaacaga aattatatgt aaataaaata ataataatat ggtttccata     420
ctctatagca tatcatatgg tgcattgcac atatttcatc gacaaagaaa gccacggtgc     480
agacgctcga ttttgacatt ttacaactta caaggccatg atcagatcga taataccaaa     540
tggtaccacc taactaggtg atatatatta tgtatgtcat tattttaaac tgtattacaa     600
agactatttt ttcattaatt ggtacaaaga aaaattaaac agaaaagaaa ggaaaaaatg     660
actcaccacc tagcacctag acacctagac accaagtacc caaaccctct attttcaaca     720
tctattttca gatgtaaata tgagttggac gaagaaggtg ttagcaatta tttgattaat     780
cttgctacga taattatgat ccactcactt agtcattttt tcagaccaa gacaactagc      840
ttgagttttt tattgtatgt ggtcggaacg ttttttgtaa ttaaaaaaat aaaagttgca     900
tcattatata tggtagatta agtaattgat caatcaacgt ttaattttgc atttatcggc     960
aaggtggagg ttcnaacttc cagtcgaact tagagagtca ttggagacct tgaccagtta    1020
actagcggtg tcgaaaacct gcacaacttg agatttaatt gcatacccttt tatatatgac    1080
gcgtttatt tttttttcct agaaaataat ttggaagaaa ataagaatat gtattctgtg     1140
aaagctaggc caaaacgaat gtcttttcgt cgttttcgtt aaaggtttag atcatatttc    1200
atctggtcca acactcaaac ttgtataatg gacgaattat tagtcatttt agacctaccg    1260
gctagcgcga ctttttttgtt ttccataaag attcgataat tgcatggcca gatgcaaagt    1320
ttgaaattta atgtttgcca aatcctatca tacaccacaa cacatgtctc agggccaagt    1380
ggcaccagca acattcctg tcataattaa tttttttaat gagaaggagg aaactcacag    1440
ctattactcg aaggtatata atattgagta aatcttactt tgtgattcta gttgacaaaa    1500
caccgcaaga taaactatac taagttcaaa tcacctcacc gggttggctc agattggttt    1560
tttcaataca agagggggtg tgaactcccg tgccgacctc ttttgaggga caataatgta    1620
cggtcacgcc aaccaagctt gatttttttnt gacaaatata ttactacata tattacacgg    1680
tcaaataatt aatcaaaaaa taaaaaaaga ccccaattaa agtccccaac cactctcaaa    1740
tattctatt aagggaaacc ttagaggcaa ttcatgcatc ctcaacccct tcttcttcat     1800
tttcttaatc ttacatttttc ctttgaccat ggcttccatt gtgagtcggc tcagtcttgc    1860
gctaagcctc atagctctag ctctagctgg ctactccatt taccagcaca cacagtcagc    1920
```

```
catggagagc cagcccatca aggctctccc ggcgtggcta cagctcccca cgttccaatc    1980
tgccaacgtg ttatcgtatt atccgagtgg ccgcaaatcc tcccccgccg gcatgctttc    2040
cgacgaagct tgcgtgttct ccgccgttaa agaagttgtc gacgccgcca tcgataacga    2100
aactcgcatg ggggcttccc tcattcgtct cttcttccac gattgctttg tcgatgtacg    2160
tatagtatac atataattat gtaaaaccta tatatatata tatatatata tatatacatg    2220
cacaaaaagt ttataatact aatatatacc catacttttt gcatatcatt atatatatta    2280
acacgattat attaaaaacc aataatatat tatatatata tatatagtta actatctttt    2340
ctttcacttt cttatcactt tttaaattgt taaatctaaa aattaattgt tattttattg    2400
aattttttct attttctatt ttgtttaaag acttaattat actattattt aactgggctg    2460
gtaactttcc gtcaatattg tttatttaac aattgtaaca attaaaacca attgtaacaa    2520
tagtacgtaa aagatcaaag tgacataaac cagcttaagt tttttaaatg gacgaactca    2580
aaacaaaaaa gtcaatatgt aatttcggta gagaagtcaa atttaaaatt tcatagttat    2640
caaatcaatt gttttatcaa cccagctagg ttgnctattt caaaaactaa ttagacattg    2700
gtgtgcatga acattacgt taaaacaaaa gtcatcaccc acctcgtctt ataattggtg    2760
tacctaagtt atcacacgtt cctgtcgaac ttacacgcca aacatgtcaa tatgtcaaat    2820
gctttaatga aaaatattat tagattatta tttatctaat actaaatttt cttcttcgta    2880
aaaatttgtg tgtattaggt tgtgatgcag ggcttctttt gaatgatacg gcgacgttca    2940
caggggaaca aactgcattt ggcaatctta attccgtgag agggtttgag gttatagaac    3000
aagctaaaca gaatgcagta gctaaatgtg ccgatacacc cgtatcttgt gctgacattt    3060
tatctattgc tgctcgtgat tctttcgaac gggtaagtct tcaatatcgt gtataagtgt    3120
tactaataat gtcaatatgt tacatgtaga catgtatttta tttatttttct ttgtatttac    3180 attcaacagt ttagtggagc aacatacact gtgactttag ggcgactcga tgcgagaacc    3240
gcgaacttaa ccggagctaa tacccagctt gtcggaccat cggaaaactt gactgaacaa    3300
gtcaggaaat ttggcatcaa aggatttaac gagagggaat tggtcgcctt gttgggttca    3360
cacacgctag ggtttgccag atgtccggtt ttatgtgaca acagaaacat taacccggtt    3420
cgggtccccg gtctgcaatg caactgtcct gtaactaata ctgacccggg tttggtcggg    3480
ctggacccca cacccgatac attcgaccaa cgttattact ctgacctagt cagcggccaa    3540
ggcctcctgt tttccgacca acagctgatg aacagcacca ccaccagcga cgccgtgacg    3600
acgtaccgtg actccataga caccttcctt gccgacttcg ccgccgccat ggtcaagatg    3660
agcaacctgc ctccgtccgc cggagttgag ctcgaaatcc gtgacgtctg cagccgggtg    3720
aatgacgtct ctgttgcatc cg                                             3742
```

<210> SEQ ID NO 2
<211> LENGTH: 1828
<212> TYPE: DNA
<213> ORGANISM: Imopoea batatas
<220> FEATURE:
<221> NAME/KEY: misc_feature
<222> LOCATION: (0)...(0)
<223> OTHER INFORMATION: n = a, t, c, or g

<400> SEQUENCE: 2

```
ttaatttcaa tattttgtct gtattttttt tttagtacta ctcatgtcaa atcctgttac      60
atataaaata tgttcaaatt cactgaaact caaatctata acctcttatt tgatagagtc     120
```

-continued

```
actctataca actagaccac ggaattgtca actagaccac ggaattgtta gcttgtttat      180
tgtattcacg tataattttg atgaatatca tcaactttga cgggcaaaat agatagcatg      240
tggcggccac agtttcaaaa ttcatacaag atgtcaaggg gaccggcccg gtggctgcgt      300
gcatatcacg tgcaagattt gtgaaattct ttctagattc cttttatcct tttcttcttt      360
cttgaaaaaa tagaaacaga aattatatgt aaataaaata ataataatat ggtttccata      420
ctctatagca tatcatatgg tgcattgcac atatttcatc gacaaagaaa gccacggtgc      480
agacgctcga ttttgacatt ttacaactta caaggccatg atcagatcga taataccaaa      540
tggtaccacc taactaggtg atatatatta tgtatgtcat tattttaaac tgtattacaa      600
agactatttt ttcattaatt ggtacaaaga aaaattaaac agaaagaaa ggaaaaaatg       660 actcaccacc tagcacctag acacctagac accaagtacc caaaccctct attttcaaca      720
tctattttca gatgtaaata tgagttggac gaagaaggtg ttagcaatta tttgattaat      780
cttgctacga taattatgat ccactcactt agtcattttt ttcagaccaa gacaactagc      840
ttgagttttt tattgtatgt ggtcggaacg ttttttgtaa ttaaaaaaat aaagttgca       900 tcattatata tggtagatta agtaattgat caatcaacgt ttaattttgc atttatcggc      960
aaggtggagg ttcnaacttc cagtcgaact tagagagtca ttggagacct tgaccagtta     1020
actagcggtg tcgaaaacct gcacaacttg agatttaatt gcataccttt tatatatgac     1080
gcgttttatt ttttttttcct agaaaataat ttggaagaaa ataagaatat gtattctgtg    1140
aaagctaggc caaaacgaat gtcttttcgt cgttttcgtt aaaggtttag atcatatttc     1200
atctggtcca acactcaaac ttgtataatg gacgaattat tagtcatttt agacctaccg     1260
gctagcgcga cttttttgtt ttccataaag attcgataat tgcatggcca gatgcaaagt     1320
ttgaaattta atgtttgcca aatcctatca taccacaca cacatgtctc agggccaagt      1380
ggcaccagca acattcctg tcataattaa ttttttttaat gagaaggagg aaactcacag     1440
ctattactcg aaggtatata atattgagta atcttactt tgtgattcta gttgacaaaa      1500
caccgcaaga taaactatac taagttcaaa tcacctcacc gggttggctc agattggttt     1560
tttcaataca agaggggggtg tgaactcccg tgccgacctc ttttgaggga caataatgta    1620
cggtcacgcc aaccaagctt gattttttnt gacaaatata ttactacata tattacacgg    1680
tcaaataatt aatcaaaaaa taaaaaaga ccccaattaa agtccccaac cactctcaaa      1740
tattctattt aagggaaacc ttagaggcaa ttcatgcatc ctcaacccct tcttcttcat     1800
tttcttaatc ttacattttc ctttgacc                                        1828
```

<210> SEQ ID NO 3
<211> LENGTH: 12
<212> TYPE: PRT
<213> ORGANISM: Imopoea batatas

<400> SEQUENCE: 3

Asn Asn Asn Ser Ala Cys Gly Thr Gly Asn Cys Met
  1               5                  10

<210> SEQ ID NO 4
<211> LENGTH: 27
<212> TYPE: DNA
<213> ORGANISM: Artificial Sequence
<220> FEATURE:
<223> OTHER INFORMATION: forward primer 1

<400> SEQUENCE: 4

-continued acgcgtcgac cttactttgt gattcta                    27

<210> SEQ ID NO 5
<211> LENGTH: 28
<212> TYPE: DNA
<213> ORGANISM: Artificial Sequence
<220> FEATURE:
<223> OTHER INFORMATION: forward primer 2

<400> SEQUENCE: 5
acgcgtcgac aatggacgaa ttattagt                   28

<210> SEQ ID NO 6
<211> LENGTH: 26
<212> TYPE: DNA
<213> ORGANISM: Artificial Sequence
<220> FEATURE:
<223> OTHER INFORMATION: forward primer 3

<400> SEQUENCE: 6
acgcgtcgac ggtcggaacg tttttt                     26

<210> SEQ ID NO 7
<211> LENGTH: 27
<212> TYPE: DNA
<213> ORGANISM: Artificial Sequence
<220> FEATURE:
<223> OTHER INFORMATION: forward primer 4

<400> SEQUENCE: 7
acgcgtcgac ccatgatcag atcgata                    27

<210> SEQ ID NO 8
<211> LENGTH: 27
<212> TYPE: DNA
<213> ORGANISM: Artificial Sequence
<220> FEATURE:
<223> OTHER INFORMATION: forward primer 5

<400> SEQUENCE: 8
acgcgtcgac aatattttgt ctgtatt                    27

<210> SEQ ID NO 9
<211> LENGTH: 22
<212> TYPE: DNA
<213> ORGANISM: Artificial Sequence
<220> FEATURE:
<223> OTHER INFORMATION: reverse primer 1

<400> SEQUENCE: 9
cgggatccgg tcaaaggaaa at                         22

<210> SEQ ID NO 10
<211> LENGTH: 19
<212> TYPE: DNA
<213> ORGANISM: Artificial Sequence
<220> FEATURE:
<223> OTHER INFORMATION: NPTII primer 1

<400> SEQUENCE: 10
gaggctattc ggctagatg                             19

<210> SEQ ID NO 11
<211> LENGTH: 21
<212> TYPE: DNA
<213> ORGANISM: Artificial Sequence

```
<220> FEATURE:
<223> OTHER INFORMATION: NPTII  primer 2

<400> SEQUENCE: 11
atcgggagcg gcgataccgt a                                                    21

<210> SEQ ID NO 12
<211> LENGTH: 18
<212> TYPE: DNA
<213> ORGANISM: Artificial Sequence
<220> FEATURE:
<223> OTHER INFORMATION: promoter  primer 1

<400> SEQUENCE: 12
ccattgatca gatcgata                                                        18

<210> SEQ ID NO 13
<211> LENGTH: 19
<212> TYPE: DNA
<213> ORGANISM: Artificial Sequence
<220> FEATURE:
<223> OTHER INFORMATION: promoter  primer 2

<400> SEQUENCE: 13
ggtcaaagga aaatgtaag                                                       19
```

PEROXIDASE GENOMIC GENE DERIVED FROM *IPOMOEA BATATAS* AND A PROMOTER THEREOF

FIELD OF THE INVENTION

The present invention relates to a stress inducible promoter. Particularly, it relates to a new genomic gene coding a peroxidase isoenzyme of *Ipomoea batatas* and a promoter thereof whose expressions are strongly induced under environmental stresses in the cultured cells and whole plants.

The whole or part of the peroxidase gene promoter of the present invention can be effectively used to develop stress-tolerant plants, resistant to the environmental stresses, and to develop transformed organisms producing useful materials on a large scale.

BACKGROUND

When the most organisms including plants are exposed to various environmental stresses generated according to the environmental aggravation of earth as well as biological stress of bacteria, insect and virus, oxygen which is necessary for keeping life changes into reactive oxygen species of superoxid anion radical, hydrogen peroxide and hydroxyl radical that induce serious physiological disorder. Therefore, there are many systems in the body to get rid of these reactive oxygen species such as the macromolecular anti-oxidative enzymes of superoxide dismutase (SOD), peroxidase (POD) and catalase (CAT) and small molecular anti-oxidative materials of vitamin C, vitamin E and glutathione.

It has been well known that peroxidase widely exists in plant cells as a reducing enzyme which reduces hydrogen peroxide in the presence of electron donor. Peroxidase is becoming the center of interest since it has an important role for plant to react on the various external stresses and is an industrially important enzyme by being used as various clinical test reagents because of its sensitive enzyme reaction. Generally, the activity of plant peroxidase is increased by the various environmental stresses and, particularly, is very high in the cultured cells which are considered to be grown under the high oxidative stress. It has been reported that the cultured cell of *Ipomoea batatas* produces peroxidase on a large scale than any other cultured cells of plant (Phytochemistry, 39, 981–984, 1995).

The genes coding peroxidase isoenzymes of the some plants that are originated from about 20 species plants of horseradish, barley, wheat, rape, tobacco, spinach and rice have been reported. The present inventors have isolated the peroxidase gene of *Ipomoea batatas* for the first time. We have reported that the anionic peroxidase swpa1 and neutral peroxidase swpn1 isolated from the cultured cells of *Ipomoea batatas* are specifically expressed in the cultured cells and stem of *Ipomoea batatas*, and plurally exist in genome (Mol. Gen. Genet., 255, 382–391, 1997). It has also reported that peroxidase can be produced on a large scale by transforming the whole or part of these peroxidase genes to plant organisms and cells (*Phytochemistry*, 47, 695–700, 1998; *Phytochemistry* 48, 1287–1290, 1998).

In addition, the present inventors have found out the nucleic acid sequence of the anionic peroxidase gene swpa2 (GeneBank Accession NO. AF109124) and swpa3 (GeneBank Accession No. AF109123) from *Ipomoea batatas*. According to this, swpa2 has 71 signal peptides, swpa3 has 66 signal peptides, and swpa2 and swpa3 have 1245 and 1310 bp of nucleic acid sequences coding 358 and 349 of amino acids, respectively. The isoelectric point of mature protein expressed by swpa2 and swpa3 is 4.1 and 4.3, respectively, and this shows that all the genes code the anionic peroxidase. AAUAA of typical polyadenylation signal and poly(A)-tail exist in the 3'-untranslated region of swpa2 and swpa3, and particularly, the N-terminal sequence of swpa2 gene is completely same as that of major isoenzyme (A-2) from the cultured cells of *Ipomoea batatas*. In addition, the present inventors have demonstrated that swpa2 gene is strongly expressed in response to wounding, low temperature or ozone treatment in the leaf of *Ipomoea batatas*, on the other hand, swpa3 gene is weakly expressed in response to wounding, but strongly expressed by low temperature or ozone treatment (*Mol. Gen. Genet.*, 261, 941–947, 1999).

SUMMARY OF THE INVENTION

It is an object of this invention to provide a genomic peroxidase DNA originated from *Ipomoea batatas* and nucleic acid sequence thereof.

It is a further object of this invention to provide a promoter of which expression is strongly induced by the various environmental stresses.

It is an additional object of this invention to provide transformed organisms that are resistant to the various environmental stresses and a preparing method thereof.

It is also an object of this invention to provide transformed organisms that are capable to produce useful materials on a large scale and a preparing method thereof.

BRIEF DESCRIPTION OF THE DRAWINGS

FIG. 2a shows nucleic acid sequences of the genomic gene SWPA2 coding peroxidase of *Ipomoea batatas* of the present invention and amino acid sequences coded therefrom.

FIG. 2b is continued from the nucleic acid sequences of genomic DNA SWPA2 coding peroxidase and the amino acid sequences coded therefrom of the FIG. 2a.

FIG. 3 shows nucleic acid sequences of the promoter of genomic DNA SWPA2 coding peroxidase of *Ipomoea batatas*.

FIG. 7a shows a result measuring the induced GUS activity in the absence of wounding to the transformed tobacco plants which are introduced with the promoter deletion mutants of the present invention.

FIG. 7b shows a result measuring the induced GUS activity in the presence of wounding to the transformed tobacco plants which are introduced with the promoter deletion mutants of the present invention.

| A; pBS1314 | B; pBS1824 |
|---|---|
| C; control | D; pBI121 |

Figure 10A:
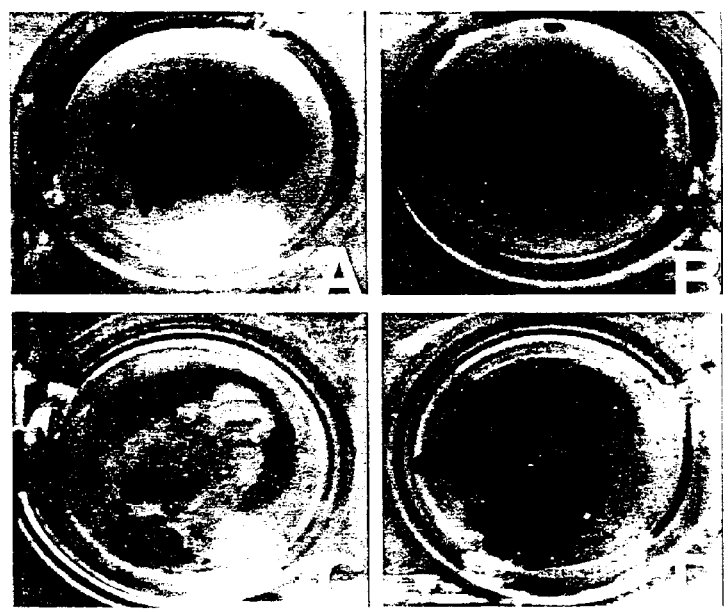
FIG. 10a shows the callus induced from the transformed tobacco plants which are introduced with the promoter deletion mutants of the present invention after GUS staining.
Figure 10B:
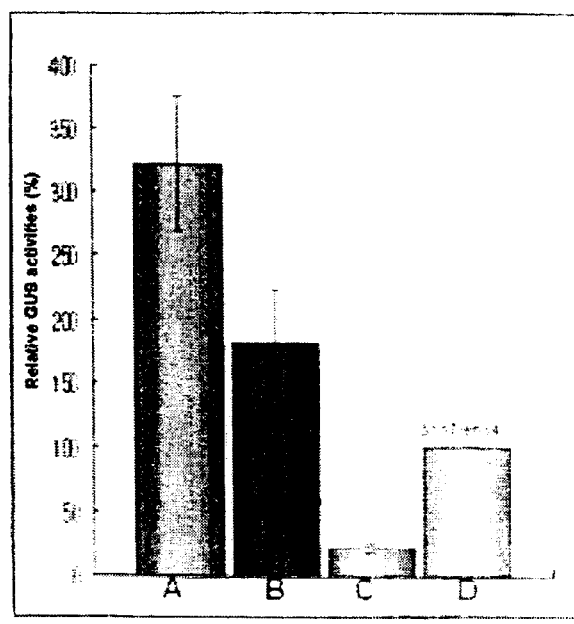

FIG. 10b shows results measuring the GUS activity of the callus induced from the transformed tobacco plants which are introduced with the promoter deletion mutants of the present invention.

| A; pBS1314 | B; pBS1824 |
|---|---|
| C; control | D; pBI121 |

Figure 11A:
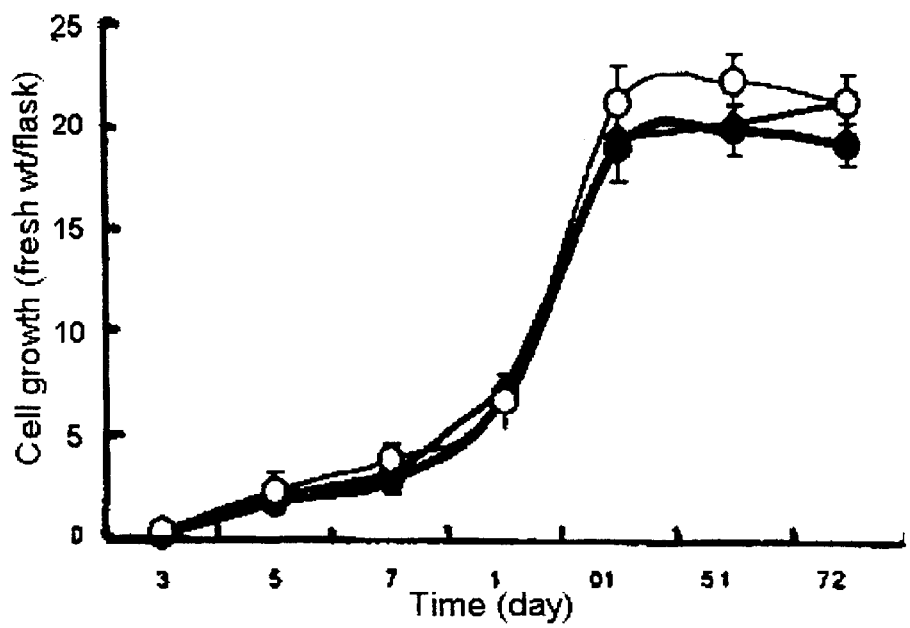

FIG. 11a shows a cell growth curve of the suspension cultured cells induced from the transformed tobacco plants which are introduced with the promoter deletion mutants of the present invention.

Figure 11B:
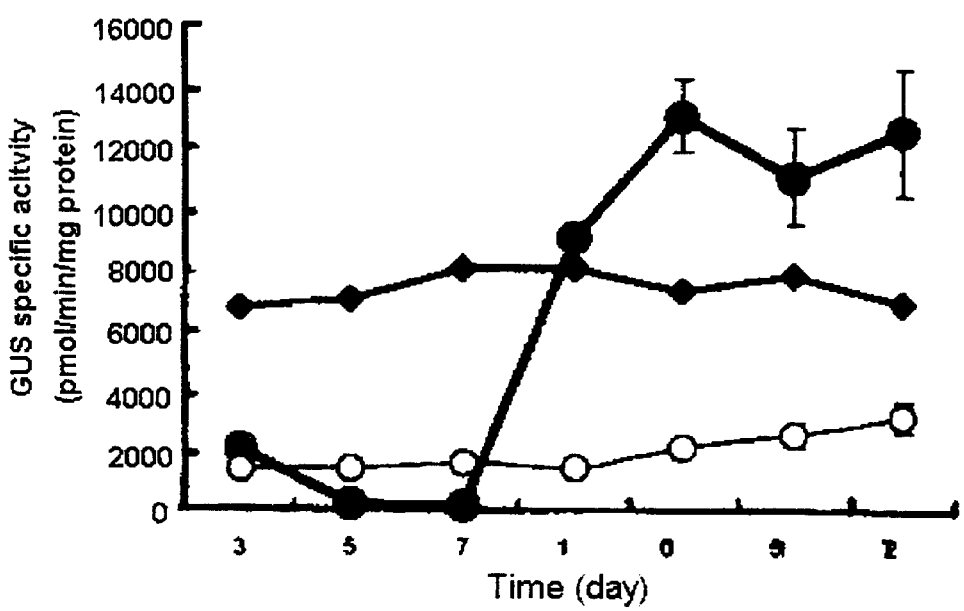

FIG. 11b shows a result of measuring the GUS activity of the suspension cultured cells induced from the transformed tobacco plants which are introduced with the promoter deletion mutants of the present invention.

DETAILED DESCRIPTION OF PREFERRED EMBODIMENTS

A terminology and technology referred in the present detailed description are used as general meaning of the technical field which includes the present invention. In addition, references mentioned in the present detailed description are all included in the present detailed description for describing the present invention.

"Derivatives of nucleic acid sequences" of the present invention mean modified nucleic acid sequences by substitution, deletion or addition of one or more base in the nucleic acid sequence of swpa2, SWPA2 or SWPA2 promoter with keeping its biological activity.

"Derivatives of proteins" of the present invention mean modified amino acid sequences by substitution, deletion or addition of one or more amino acid in the amino acid sequence coded by swpa2 with having peroxidase activity.

"SWPA2 promoter" means a nucleic acid sequence which includes the nucleic acid sequence represented by the SEQ. ID NO.2 and gives a transcription activity to genes operably linked thereto under the appropriate condition.

"Active fragment of SWPA2 promoter" means a nucleic acid sequence which includes the part of nucleic acid sequence represented by the SEQ. ID NO.2 and gives SWPA2 promoter activity to genes operably linked thereto.

"Transformed organisms" mean transformed cells or plants that are transformed with the DNA construct comprising SWPA2 promoter operably linked to a DNA sequence coding for a heterologous protein. The transformed organisms of the present invention include transformed microorganisms, animal cells, plant cells, transgenic animals or plants and cultured cells derived from them.

"Environmental stress" means biotic or abiotic stresses such as wounding, reactivate oxygen species, tumor, heat, moisture, temperature, salt, air pollution, UV, heavy metal, et al. which functions to objective organism as a stress.

Hereinafter, the present invention is described in detail.

The present invention provides the genomic gene SWPA2 coding peroxidase originated from *Ipomoea batatas* and nucleic acid sequence thereof.

The SWPA2 of the present invention comprises the whole or part of nucleic acid sequences represented by the SEQ. ID NO.1, wherein the DNA sequence includes exons coding peroxidase swpa2 of *Ipomoea batatas*.

The SWPA2 is a genomic clone having the same ORF (open reading frame) as swpa2 by third screening from the genomic DNA library of *Ipomoea batatas* and named as natural SWPA2 (see FIG. 2).

The natural SWPA2 comprises 3 exons, 2 introns and promoter region, and the nucleic acid sequences of its exons are completely same as those of swpa2 cDNA (Gene Bank Accession No. AF109124). The peroxidase genomic clone of *Ipomoea batatas* comprises considerably long intron that, especially, the first intron of them is 737 bp. It is longer than 100–300 bp of intron in any other plant. The each intron of the peroxidase genomic clone follows GT-AG rule which 5' end of intron starts with GT and 3' of intron ends with AG.

In addition, the present invention provides the promoter of which expression is induced by various environmental stresses.

In this specification, SWPA2 promoter is used as the meaning including SWPA2 promoter and an active fragment thereof unless any special limitation is described. SWPA2 promoter of the present invention comprises the whole or part of nucleic acid sequences represented by the SEQ ID NO:2 having promoter activity. For an example, SWPA2 promoter preferably comprises 515 to 1828 of nucleic acid sequence represented by the SEQ ID NO:2 or the part DNA sequence thereof having promoter activity.

The promoter according to the present invention is strongly expressed by environmental stresses and derived from the natural SWPA2 of genomic peroxidase gene of *Ipomoea batatas*.

The natural SWPA2 has promoter region in the upstream of translation initiation site and is named as SWPA2 promoter. The characteristics on the nucleic acid sequence of SWPA2 promoter are analyzed by Transcription Element Search Software (TESS) of Computational Biology & Informatics Laboratory. As a result, SWPA2 promoter comprises nucleic acid sequences represented by the SEQ. ID NO.2, and has CAAT box on −895 position and TATA box for transcription initiation (see FIG. 3).

As a result of sequence analysis, it has been found that SWPA2 promoter contained regulatory elements of eucaryotic promoter, i.e. TATA box for transcription initiation and CAAT box at −895 position. In addition, SWPA2 promoter has a similar motif to G box represented by NNNSACGT-GNCM at −445 to −455 region which is a binding site of transcriptional regulatory protein and regulated by ABA (abscisic acid), methyl jasmonate, UV, wounding and hypoxia (Williams, M. et al., 1992) (see FIG. 3). Transcription factor SP-1 which is expressed tissue specifically and can be induced by stress, exists between G box of SWPA2 promoter and transcription initiation site. Furthermore, 6 repeat sequence of AAAATAA was found in the SWPA2 promoter region.

SWPA2 promoter also has heat shock element (HSE) containing consensus sequence of AGAAN at −1170 to −1188 region (see FIG. 3). GCN-4 and AP-1 has been known to respond reactive oxygen species, and especially AP-1 is known as essential element to respond nitrogen at C-hordein promoter of barley (Muller, M. et al., 1993). In addition, there are oct-1 and C/EBP beta for enhancer element in SWPA2 promoter. GCN-4 is in the three places and AP-1 in the two places. Especially, there are inverted repeat sequences of GCN-4 and AP-1 between −1175 and −1163 region (see FIG. 3)

The expression of SWPA2 promoter of the present invention is strongly induced by various external factors including oxidative stress. Particularly, since it is strongly induced in cultured cell, SWPA2 promoter of the present invention can be useful for the development of environmental stress-tolerant plants and the production of useful materials using transformed plant cells.

The SWPA2 promoter of the present invention can effectively induce the expression of gene by stresses. For this, the promoter of the present invention comprises various transcription factors which recognize the stresses by ABA, methyl jasmonate, wounding, hypoxia, heat or nitrogen. By using these characteristics, it can be used for manufacturing fusion gene construct which comprises DNA sequence having promoter activity and structural gene operably linked to this DNA sequence. Since the fusion gene construct comprises the structural genes related to the production of useful materials and SWPA2 promoter gene, and expresses the useful material by regulation of SWPA2 promoter under various environmental stresses, it can be useful for manufacturing transformed organisms for the production of useful material. In addition, if the structural genes are related to various environmental stress resistance in the fusion gene construct, it can be used for manufacturing stress-tolerant organisms which are resistant to external stress.

The promoter of the present invention is functional in microorganism as well as plant, and therefore, it can be used for developing transformed plant cells, transformed plants and transformed callus derived therefrom, transformed microorganisms and transformed animal cells.

In addition, the present invention provides a preparing method of transformed organisms using the SWPA2 promoter which can induce the production of useful material by various environmental stress.

The preparing method of transformed organisms comprises the steps of;

1) constructing an expression vector which comprises the first DNA sequence representing promoter activity which comprises nucleic acid sequence represented by the SEQ. ID NO.2 or the part thereof operably linked to the second DNA sequence coding the heterologous protein,
2) introducing the expression vector into a host cell; and
3) selecting the host cell introduced with the expression vector.

In the preparing method of the present invention, the useful material contains various proteins or peptides representing pharmacological effect and a material endowing stress resistance to transformants. Therefore, the preparing method of the present invention is used for developing stress-tolerant organisms and producing the useful materials in transformed organisms.

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Analysis of Peroxidase Genomic DNA

To find genomic DNA of peroxidase gene swpa2, the present inventors performed Southern blot analysis of swpa2 gene to confirm that it actually existed in the *Ipomoea batatas* genome. 15 μg of genomic DNA was extracted by the method of Dellaporta et al. (Dellaporta, Newsletter, 57, 26–29, 1983), from the cultured cells of *Ipomoea batatas*, digested with restriction enzymes EcoRI, HincII and HindIII, and performed agarose gel electrophoresis. After transferring genomic DNA on the gel to the nylon membrane, hybridization was carried out using the gene fragment labeled with $^{32}$P at the specific 3'-end untranslated region of swpa2 gene (FIG. 1).

Figure 1:
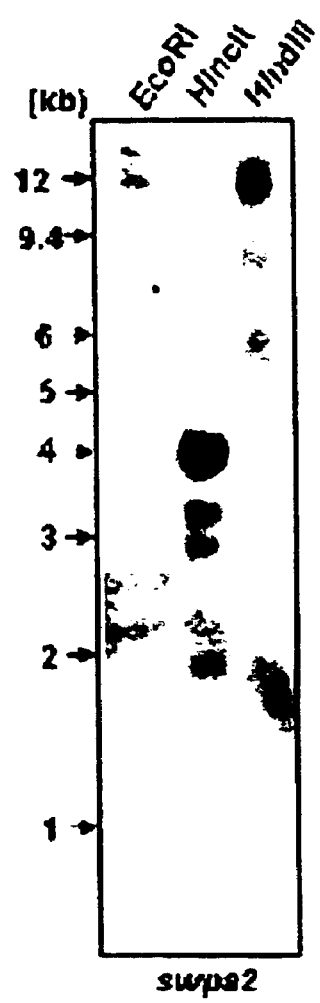
FIG. 1 shows a result analyzed by Southern blot for isolating genomic DNA including peroxidase gene of *Ipomoea batatas* of the present invention.

As illustrated in FIG. 1, swpa2 gene was detected more than 2 bands. It implies that swpa2 gene exists plurally on the separate genome.

Example 2

Isolation and Sequencing Analysis of Peroxidase Genomic DNA

To isolate genomic DNA containing peroxidase gene swpa2 of the present invention, the present inventors performed the experiment as following.

The genomic DNA library of *Ipomoea batatas* was prepared using λ Blue STAR™ BamHI Arms vector kit (Novagen). After that, PCR was performed with swpa2-specific primer pairs using the genomic DNA library as a template. 0.5 kb of PCR product was amplified, labeled with $^{32}$P, and used for genomic DNA library screening of peroxidase in *Ipomoea batatas*. The genomic DNA library screening was carried out by the method of Sambrook et al (Molecular cloning: a laboratory manual 2ed. 1989). After third library screening, a genomic DNA clone having the same open reading frame (ORF) as swpa2 was obtained and named as natural SWPA2.

Natural SWPA2 had approximately 4 kb of nucleic acid sequence represented by the SEQ. ID NO.1 and consisted of 3 exons, two introns and its promoter region (FIG. 2). It was confirmed that the nucleic acid sequence of its exon was completely the same as that of swpa2 cDNA sequence. The first intron of peroxidase genomic clone in *Ipomoea batatas* was 737 bp in size considerably longer than other plant species of 100 to 300 bp in size, and both introns followed the GT-AG rule beginning 5'-end with GT and ending 3'-end with AG.

Example 3

Promoter Analysis of Peroxidase Genomic DNA SWPA2

The promoter of natural SWPA2 consisted of nucleic acid sequence represented by the SEQ ID NO:2 from translation initiation site to −1828 bp region of the SWPA2 gene (FIG. 3). Sequence characteristics of the SWPA2 promoter was analyzed using Transcription Element Search Software (TESS) of Computational Biology & Informatics Laboratory.

As a result of sequence analysis, it was found that SWPA2 promoter contained regulatory elements of eucaryotic promoter, i.e. TATA box for transcription initiation and CAAT box at −895 position. It was also found a similar motif to G box represented by NNNSACGTGNCM at −445 to −455 region which was a binding site of transcriptional regulatory protein and was regulated by ABA, methyl jasmonate, UV, wounding and hypoxia (Williams, M. et al., 1992) (FIG. 3). Transcription factor SP-1, which was expressed tissue-specifically and could be induced by stress, existed between G box of SWPA2 promoter and transcription initiation site. In addition, 6 repeat sequence of AAAATAA was found.

SWPA2 promoter also had heat shock element (HSE) containing AGAAN consensus sequence at −1170 to −1188 region (FIG. 3). GCN-4 and AP-1 were known to respond reactive oxygen species, and especially AP-1 was known to essential element to respond nitrogen at C-hordein promoter of barley (Muller, M. et al., 1993). In addition, there were oct-1 and C/EBP beta for enhancer element in SWPA2 promoter. GCN-4 was in the three places and AP-1 in the two places. Especially, there were inverted repeat sequences of GCN-4 and AP-1 between −1175 and −1163 region (FIG. 3).

In result, SWPA2 promoter of the present invention contained various stress-recognizing elements including reactive oxygen species and could be used for developing stress-tolerant plants, and for developing the industrial cell lines to produce useful materials under stress culture conditions.

Example 4

Preparation of Deletion Mutant of SWPA2 Promoter

Figure 4:
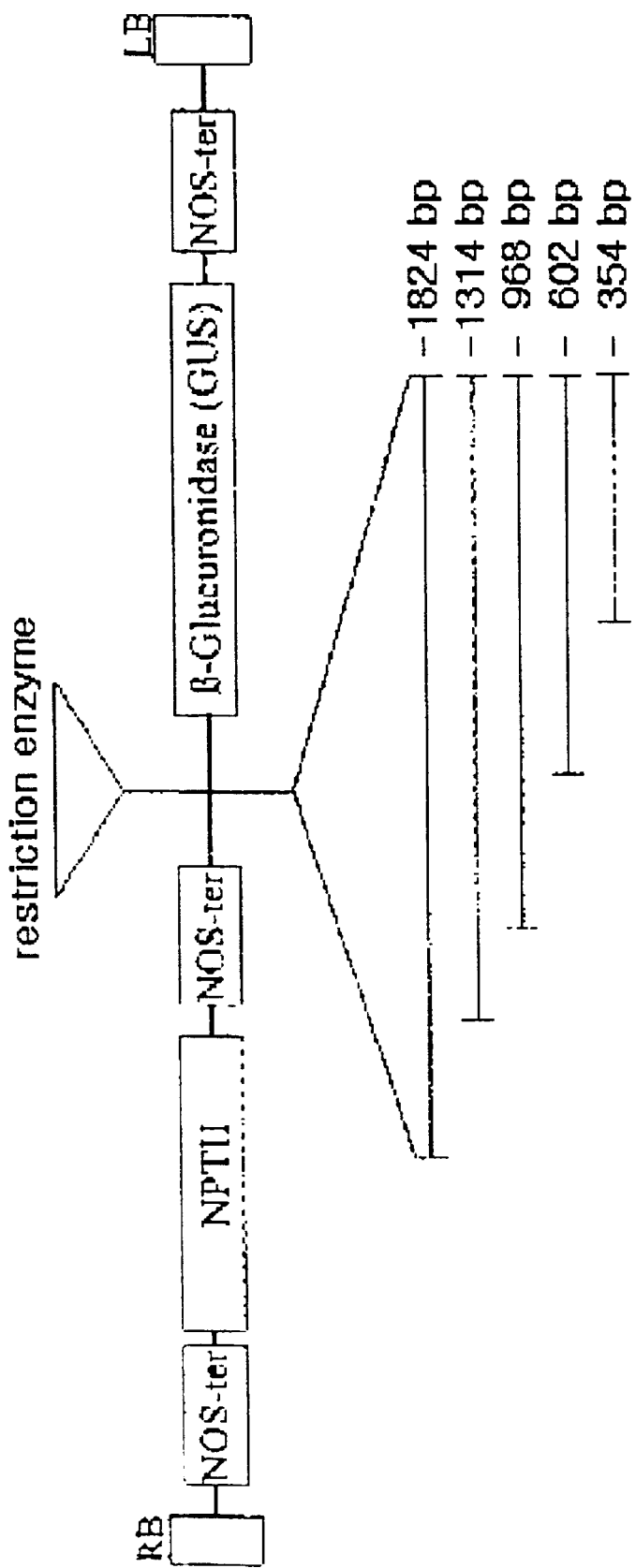
FIG. 4 shows a schematic view of preparing promoter deletion mutants of genomic DNA SWPA2 coding peroxidase of *Ipomoea batatas*.

To make deletion mutant of SWPA2 promoter, the present inventors performed PCR to amplify SWPA2 promoter region using Ex Taq polymerase (Takara) and sequence-specific primers. The sequence-specific primers consisted of upstream primers represented by the SEQ ID NO:4 to 8 and downstream primer represented by the SEQ ID NO:9. All the upstream primers were constructed to contain Sa/I restriction site and the downstream primer to contain BamHI restriction site. The deleted mutants amplified by PCR using the primer pairs were 1824, 1314, 968, 602 and 354 bp respectively (FIG. 4).

After digestion of the resulting PCR products with SalI/BamHI restriction enzyme, DNA fragments were subcloned into pBI101 plasmid vector (Clontech) which contained GUS coding region and NOS transcription terminator as binary vector. After that, plasmid vector pBS1824, pBS1314, pBS968, pBS602 and pBS354 were prepared to contain −1824, −1314, −968, −602 and −354 deletion construction, respectively, and they were used for transit assay.

Example 5

Transit Assay of SWPA2 Promoter Using Tobacco Protoplasts

Transit assay using deletion mutants of SWPA2 promoter was performed as following.

First, suspension cultured cells of tobacco BY-2 (*Nicotiana tabacum* L. cv. Bright yellow 2) were subcultured for 3 days. After that, cells were treated with enzyme solution containing 2% cellulase R-10 and 0.5% macerozyme for 3 hours to separate their protoplasts. After transfection of deletion mutant plasmid vectors prepared by the Example 4 into the protoplasts using polyethylene glycol method, the protoplasts were cultured in the darkness at 25° C. for 16 hours. Fluorescence of protoplasts containing deletion mutant plasmid vector was measured using method of Jefferson et al. (*Plant Mol. Biol. Ref.*, 5, 387–405, 1987), and promoter activities were calculated by the produced amount of GUS protein.

Figure 5:
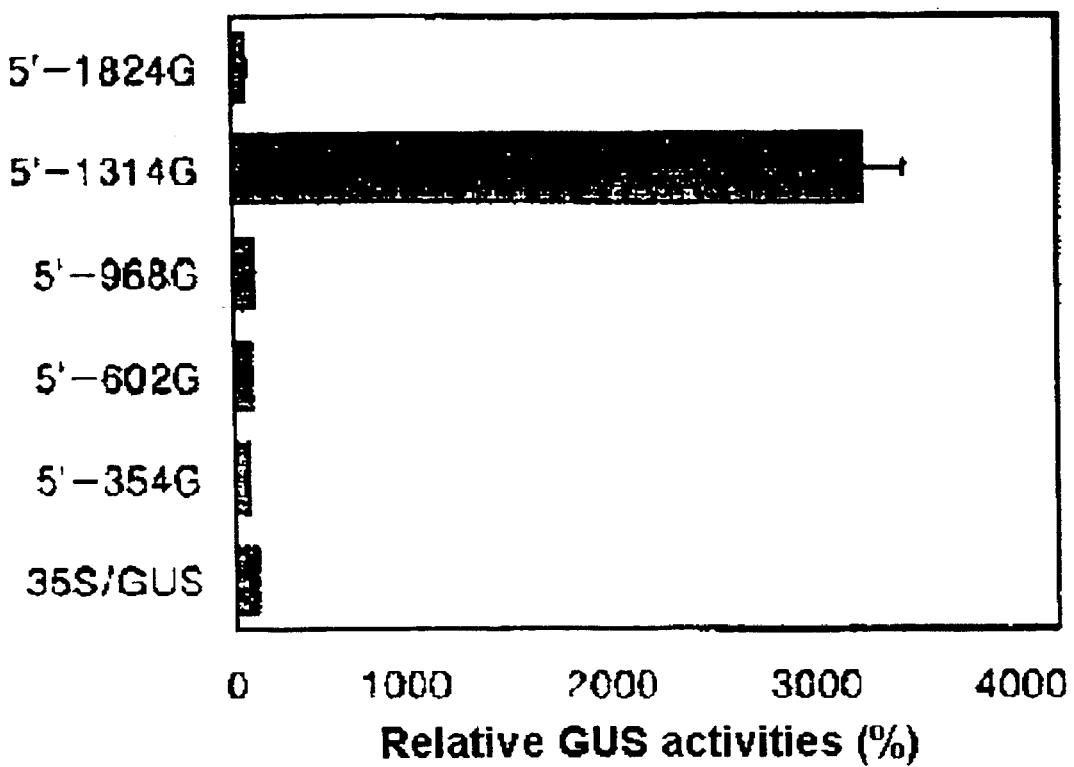
FIG. 5 shows a result of transit assay using the promoter deletion mutants of the present invention.

As a result of transit assay, it was found that especially when SWPA2 promoter containing −1314 deletion construction was used, GUS activity was increased more than 30 times compared with the case of using CaMV 35S promoter (FIG. 5).

Example 6

Expression of SWPA2 Promoter in Yeast

To investigate whether SWPA2 promoter is expressed in yeast *Saccharomnyces cerevisiae*, the present inventors used yeast/*E. coli* shuttle vector Yep352 (Hill et al., 1986) and *S. cerevisiae* L3262 as a host. Each plasmid vector containing deletion mutant of SWPA2 promoter prepared by the Example 4 which was fused with GUS gene and NOS terminator, was introduced into Yep352 vector, and was transformed into S. cerevisiae by yeast transformation method using PEG and lithium acetate. After culturing the transformed yeast in SD/URA⁻ medium (minimal SD base-UraDO (drop out) supplement, Clontech), promoter activity was investigated by measuring fluorescence generated from the transformed yeast via the same method of the Example 5.

Figure 6:
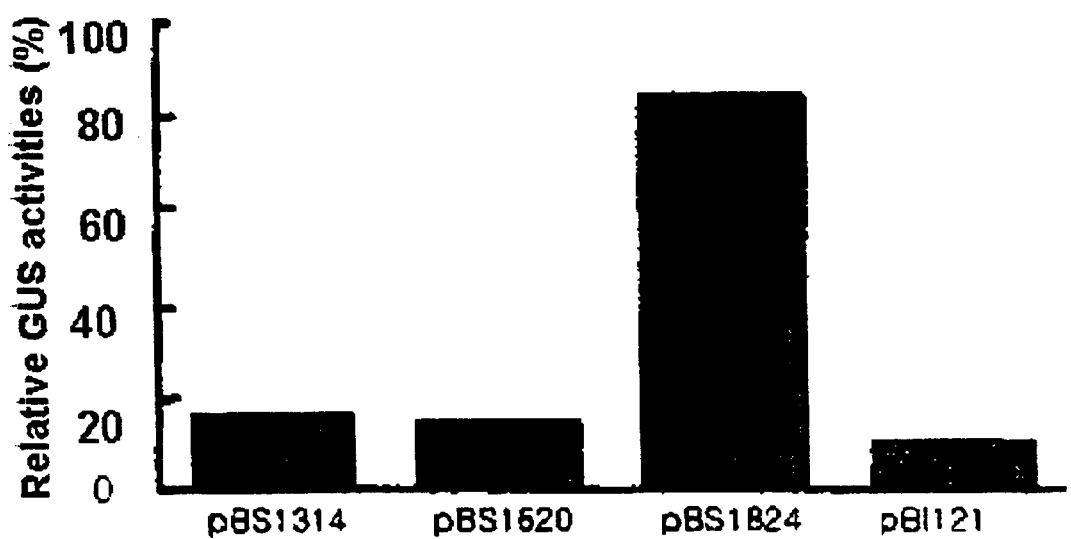
FIG. 6 shows a result measuring GUS activity of the transformed yeast which is introduced with the promoter deletion mutant of the present invention.

As a result, in case of transformed yeast introduced with −1314, −1620 and −1824 deletion construction, GUS activity was increased 1.6, 1.4 and 8.4-fold compared to that of using CaMV 35S promoter, respectively (FIG. 6).

Example 7

GUS Expression Using SWPA2 Promoter in the Transgenic Plants and its Cultured Cells <7-1> Test Plants and the Preparation of Transgenic Plants Tobacco plant (*Nicotiana tabacum* cv. Xanthi) was used for plant transformation. It was transformed with *Agrobacterium fumefaciens* LBA4404 which was introduced with plasmid vector pBS1824 (−1824 deletion construction), pBS1314 (−1314 deletion construction) containing deletion mutant of SWPA2 promoter and pBI121 containing GUS gene fused to CaMV 35S promoter, respectively. Transgenic plants were selected by culturing the transformed tobacco in MS medium (Murashige T. et al., *Physiol Plant*, 15, 473~497, 1962) containing 200 mg/l of kanamycin and 300 mg/l of claforan. After rooting and shooting step, the transgenic plants were moved into little flowerpot for growing and used for experiments.

To investigate whether the deletion mutant of SWPA2 promoter was introduced correctly into the transgenic plants, PCR was performed using NPTII primer pairs represented by SEQ. ID NO.9 and 10 and promoter primer pairs represented by SEQ. ID NO.11 and 12. In case of using NPTII primer pairs, PCR was performed 30 cycles of 95° C. for 1 min, 65° C. for 1 min and 72° C. for 1 min, and in case of using promoter primer pairs, it was performed 30 cycles of 95° C. for 1 min, 62° C. for 1 min and 72° C. for 1 min.

As a result, DNA fragment of 0.7 kb in size by NPTII primer pairs and 1.0 kb in size by promoter primer pairs were detected in the transgenic plants. Therefore, it was demonstrated that foreign genes were correctly incorporated into the transgenic plants.

<7-2> Preparation of Transformed Cell

To prepare transformed cells, the leaf of transgenic plants of which gene incorporation was confirmed by the Example <7-1>, was cultured in MS medium containing 0.1 mg/l BAP, 2 mg/l NAA and 30 g/l sucrose to induce callus formation. As a result of this, suspension culture of transformed tobacco cell line induced from the callus was established.

Transgenic tobacco cells of the present invention which was transformed with plasmid vector pBS1314 (−1314 deletion construction), was deposited at Korean Collection for Type Culture of Korea Research Institute of Bioscience and Biotechnology on Oct. 16, 2000 (Accession No: KCTC 0875BP).

<7-3> Measurement of GUS Expression in the Transgenic Plants Induced by Stress

To investigate the expression pattern of SWPA2 promoter in the transgenic plants induced in response to external environmental stress, GUS activity induced in response to stress was measured after treatment of wounding, $H_2O_2$, or UV to the transgenic plants.

First, to investigate the expression pattern of SWPA2 promoter by wounding, GUS activity was measured after hurting the transgenic plants. In result, there was no change of GUS expression in the transgenic plants introduced with pBI121 vector containing CaMV 35S promoter-GUS gene. However, in case of the transgenic plants introduced with pBS1824 and pBS1314, there was increase of GUS expression after 3 days of wounding treatment (FIG. 7). In case of pBS1314-transgenic plants, GUS expression induced in response to wounding was increased about 3.6-fold compared with untreated control plants. Although the GUS expression of pBS1824-transgenic plants was lower than that of pBS1314 transgenic plants, the expression pattern of pBS1824-transgenic plants induced in response to wounding was similar to that of pBS1314-transgenic plants.

In addition, to investigate the expression pattern of SWPA2 promoter by $H_2O_2$ treatment, 7 mm diameter of leaf disks prepared from well-grown leaf was floated on 1 mM $H_2O_2$ solution and cultured under continuous light. After cultivation, the expression pattern of SWPA2 promoter induced in response to $H_2O_2$ treatment was investigated by measuring GUS activity.

In result, after 48 hours of cultivation, the GUS expression of pBS1314-transgenic plants was increased 5.8-fold compared to untreated control and 1.7-fold compared with CaMV 35S-transgenic plants (FIG. 7). In case of transgenic plants incorporated with pBS1824 vector, GUS expression was increased 3.2-fold by $H_2O_2$ treatment and 1.2-fold compared with CaMV 35S promoter transgenic case.

Figure 8:
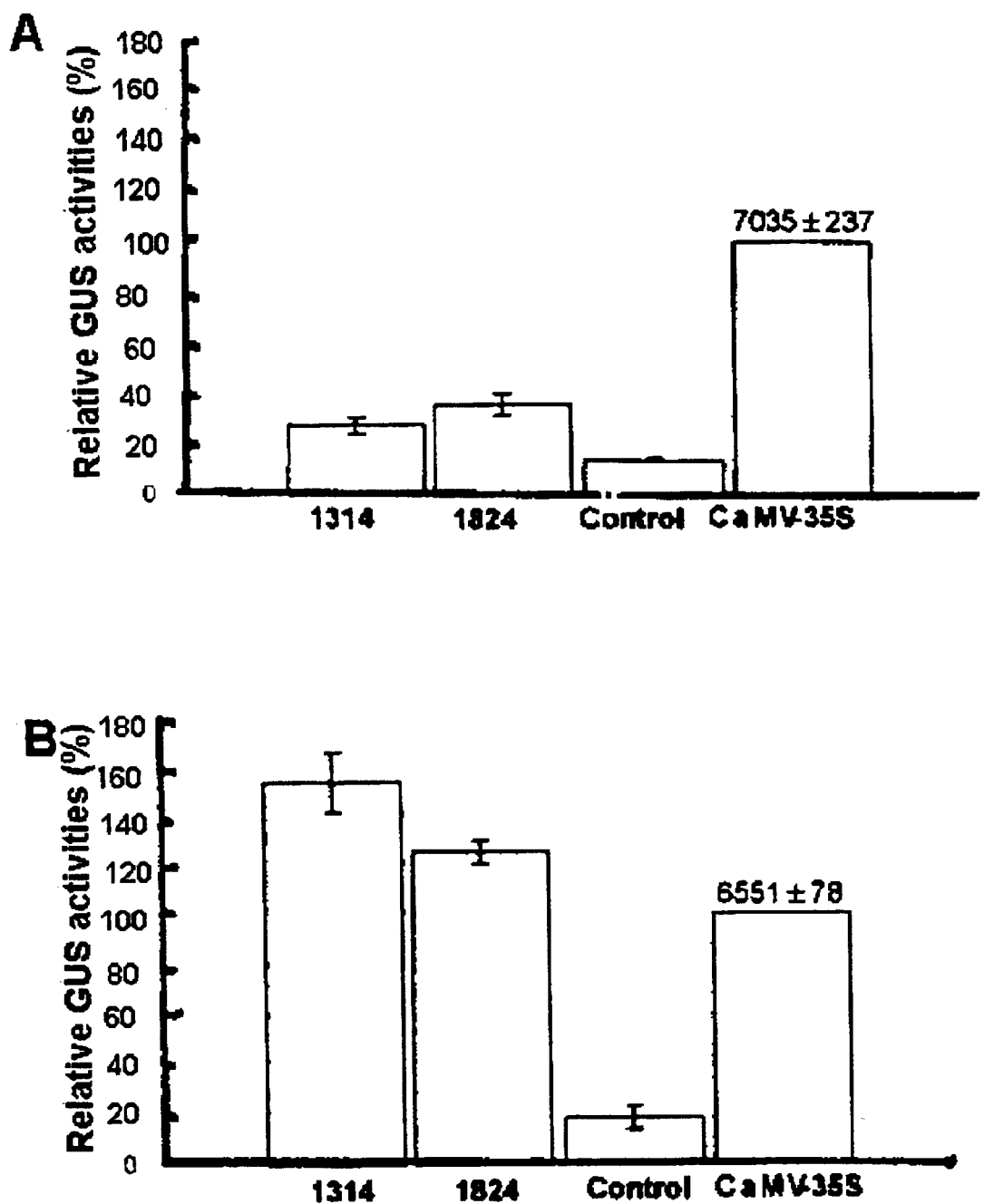
FIG. 8a shows a result measuring the GUS activity in the absence of $H_2O_2$ treatment to the transformed tobacco plants which are introduced with the promoter deletion mutants of the present invention.
FIG. 8b shows a result measuring the induced GUS activity in the presence of $H_2O_2$ treatment of transformed tobacco plants which are introduced with the promoter deletion mutants of the present invention.
Figure 9:
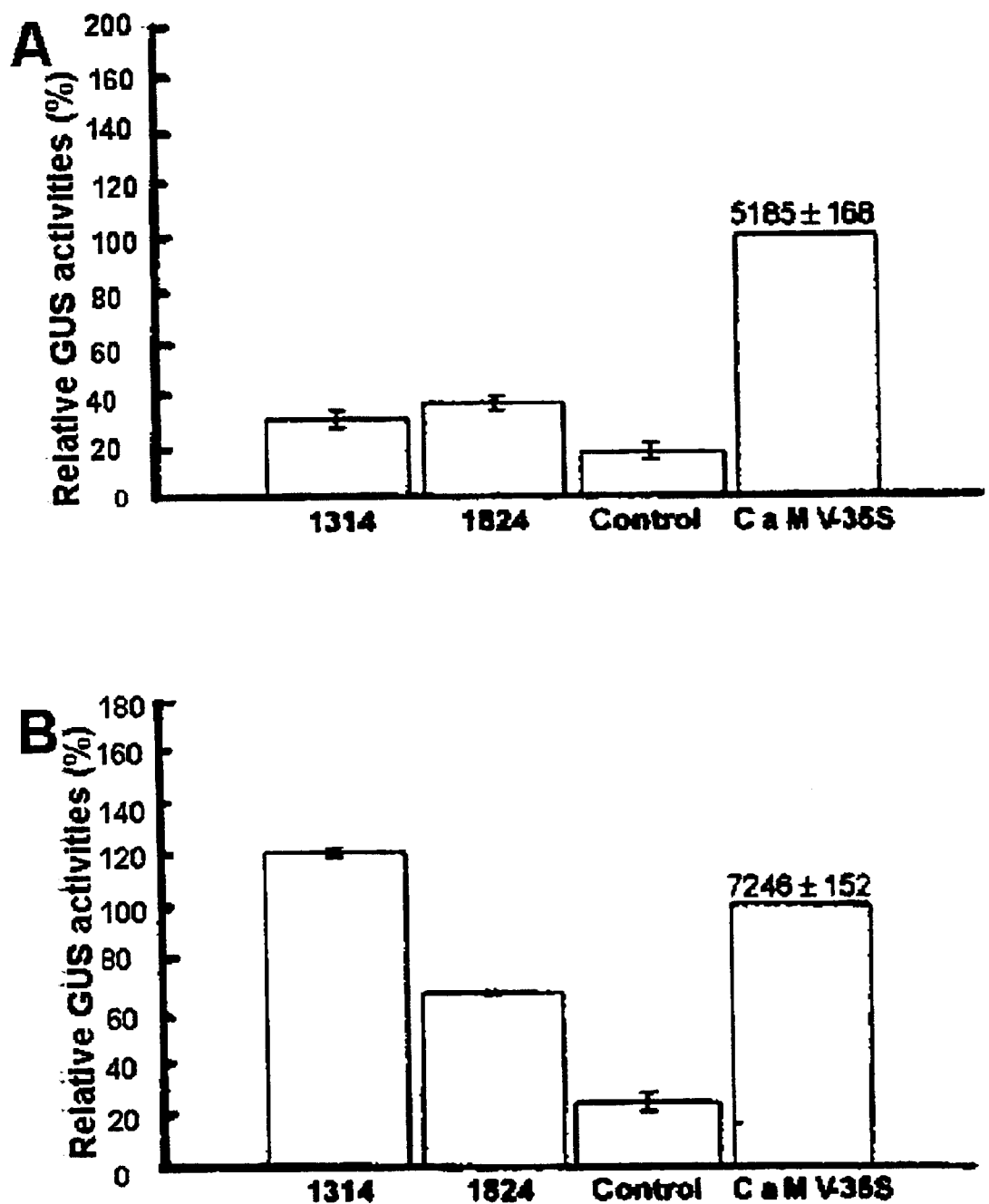
FIG. 9a shows a result measuring the GUS activity in the absence of UV irradiation to the transformed tobacco plants which are introduced with the promoter deletion mutants of the present invention.
FIG. 9b shows a result measuring the induced GUS activity in the presence of UV irradiation of transformed tobacco plants which are introduced with the promoter deletion mutants of the present invention

Furthermore, after UV irradiation onto the transgenic tobacco plants incorporated with deletion mutant of genomic peroxidase gene SWPA2 promoter, GUS activity induced in response to UV was measured. As a result, after 24 hours of cultivation, GUS activity of pBS1314-transgenic plants was increased about 5.6-fold compared with untreated control and about 1.2-fold compared with CaMV 35S promoter-transgenic plants (FIG. 8). There was 2.5-fold increase of GUS expression by UV irradiation in the transgenic plants introduced with pBS1824 vector.

<7-4> The GUS Expression of Callus and Suspension Culture

To investigate whether the expression of SWPA2 promoter of the present invention could be regulated with regard to cell growth, GUS activity of transformed callus derived from the transgenic plants which was introduced with pBS1314, pBS1824 and PBI121 vectors, respectively, was measured.

In result, pBS1314-transformed callus showed 4-fold higher GUS activity than pBI121-transformed callus (FIGS. 10a and 10b)

In addition, as a result of investigating changes of GUS activity in the suspension cultured cell derived from the transformed callus, transformed callus introduced with pBS1314, pBS1824 and pBI121 showed the same growth pattern each other and reached plateau after 15 days of cultivation (FIGS. 11a and 11b) . The pBI121-transformed cells maintained relatively low level of GUS expression irrelevant to cell growth. The pBS1824-transformed cells also maintained constant level of GUS expression irrelevant to cell growth, but showed higher GUS expression than pBI121-transformed cells. On the other hand, in case of pBS1314-transformed cells, the GUS expression was maintained lowly for 5 and 7 days of cultivation, but was increased rapidly after 7 days of cultivation. After 15 days of cultivation, maximum level of GUS expression was observed and maintained until the end of cultivation time.

INDUSTRIAL APPLICABILITY

The present invention provides a new peroxidase genomic gene SWPA2 and a promoter thereof from *Ipomoea batatas* which are expressed strongly under environmental stress conditions. The whole or part of the promoter of the present invention is used to develop stress-tolerant plants resistant to environmental stresses and transformed organisms of cells, plants, microorganisms, etc., producing useful materials on a large scale.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. An isolated DNA sequence having promoter activity, which comprises the nucleic acid sequence represented by nucleotides 515 to 1828 of SEQ. ID NO.2.

2. The DNA sequence according to claim 1, which comprises the nucleic acid sequence represented by SEQ ID NO:2.

3. The DNA sequence according to claim 1, wherein the promoter activity is induced by wounding, reactive oxygen species, or UV-light.

4. A DNA construct comprising a first DNA sequence having promoter activity which comprises the DNA sequence of claim 1, operably linked to a second DNA sequence coding a heterologous protein.

5. The DNA construct according to claim 4, wherein the first DNA sequence further contains a binding site of a transcriptional regulatory protein that recognizes stresses caused by wounding, reactive oxygen species, or UV-light.

* * * * *